United States Patent [19]

Winner

[11] Patent Number: Plant 6,636

[45] Date of Patent: Feb. 28, 1989

[54] VARIETY OF GERANIUM NAMED CARNIVAL

[75] Inventor: Blair L. Winner, Lompoc, Calif.

[73] Assignee: Denholm Seeds, Lompoc, Calif.

[21] Appl. No.: 73,808

[22] Filed: Jul. 15, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Ziesenheim & Webb

[57] ABSTRACT

A new geranium cultivar is distinguished by the substantial color contrast between the eye and the balance of the petal. The plant is compact with free and early flowering.

1 Drawing Sheet

BACKGROUND OF THE NEW PLANT

The present invention comprises a new and distinct cultivar of *Pelargonium hortorum* which is a zonal geranium known by the varietal name Carnival. The new variety (Oglevee No. Carnival, Denholm No. 50662) was discovered in a selective breeding program by Mr. Blair L. Winner. The variety was derived from the F5 generation of the F1 pink×Ivalo. The variety differs from Ivalo in flower color pattern with the spots on the petals of the new variety being larger and deeper than the parentage. The flower type is single as opposed to semi-double for Ivalo.

The new cultivar was discovered in February of 1983 at Denholm Seeds in Lompoc, Calif., was first asexually reproduced by cuttings by Denholm Seeds at Lompoc, Calif., and has been repeatedly asexually reproduced by cuttings at Oglevee Associates, Inc. in Connellsville, Pa. over a 36 month period. It has also been trial and field tested at Connellsville, Pa. yearly since the spring of 1984. It has been found to retain its distinctive characteristics through successive propagations.

The new cultivar, when grown in a glass greenhouse in Connellsville, Pa. using full natural light, 60° F. night temperature, 68° F. day temperature and 71° F. vent temperature and grown in a soilless media employing constant fertilizer of 275-300 parts per million nitrogen and potassium, has a response time from a rooted cutting to a flowering plant in a 10 cm pot of six weeks.

DESCRIPTION OF THE DRAWING

The accompanying drawing illustrates the new cultivar, the color being as true as possible with color illustrations of this type.

DESCRIPTION OF THE NEW PLANT

The Plant

Classification:
- *Botanical.*—*Pelargonium*×*hortorum.*
- *Commercial.*—Zonal geranium.

Form: Semi-dwarf; free basal branching; compact growth; flowers close to foliage; free and early flowering.

Height: 22.0-28.0 cm from media surface.

Growth: Free branching from base; short internodes.

Strength: Stands upright without artificial support.

Foliage: Stalked leaf attachment; no zoning.

Leaves:

- *Size.*—4.5-7.0 cm across.
- *Shape.*—Reniform; cordate base.
- *Margin.*—Crenate.
- *Texture.*—Pubescent; Dull (Not reflective).
- *Color.*—Top: Green group 143A. Bottom: Yellow-green group 144A.
- *Ribs and veins.*—Palmate; Yellow-green group 145B.

Petioles: 3.0-6.0 cm in length; Yellow-green group 144A.

Stem:
- *Color.*—Green group 143C.
- *Internodes.*—0.5-1.5 cm in length.

The bud:
- *Shape.*—Upright; hemispherical cluster.

Size: 2.0-3.5 cm across.

Inflorescence

Blooming habit: Continuous; upright; single heavy shatter; hemispherical in shape.

Size: 6.0-8.0 cm across.

Borne: Umbel; 2.0-3.0 cm above foliage; florets on pedicel; pedicel on peduncle.

Florets:
- *Form.*—flat to slightly cupped; round to ovate.
- *Petals.*—5 in number; separate — not united; margin entire; obovate; palmate veination; veins — insignificant.
- *Color.*—Top: Red group 55B with eyes of red-purple group 57B. Bottom: Red group 55D.
- *Size.*—3.5-4.0 cm across.
- *Texture and appearance.*—Smooth; 5 sepals per floret.

Pedicel:
- *Length.*—2.5-3.0 cm in length;
- *Color.*—Yellow green group 145B.

Peduncle: Arises from node opposite leaf petaloids; 14.0-22.0 cm in length; yellow-green group 144A.

Reproductive organs

Stamens:
- *Anthers.*—Resembles color of the center of the floret.
- *Filaments.*—White at base to purple-red at tip; irregular in shape; flat; 0.6 cm in length.
- *Pollen.*—Golden to yellow initially.

Pistils:
- *Number.*—1 with 5 parts stigma.
- *Length.*—6.0-7.0 mm.

*Stigma.—1; 5* parted at maturity; red-purple color; 2.0 mm in length.

*Style.*—1; white to pale green; 2.0 mm in length.

Ovaries: 3.0–4.0 cm in length; 1.0–2.0 mm across; pale green; very pubescent (0.1–0.5 mm in length); superior.

Fruit: None observed.

The new cultivar is characterized by the substantial contrast between the eye of the petal and the balance of the petal. The plant is compact, free and early flowering.

I claim:

1. A new and distinct variety of geranium plant, substantially as herein shown and described and parts thereof.

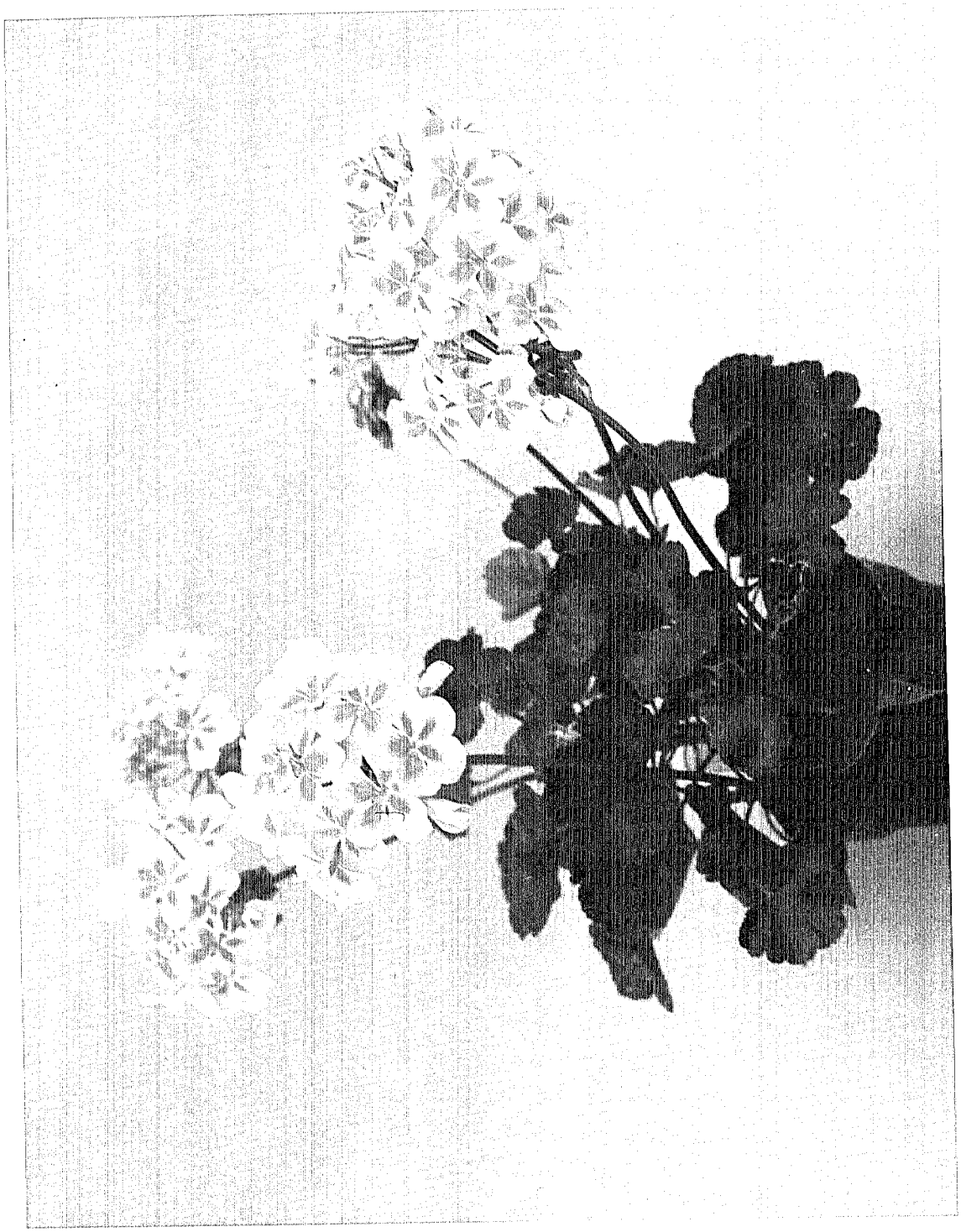

* * * * *